United States Patent [19]
Illig et al.

[11] Patent Number: 5,318,768
[45] Date of Patent: Jun. 7, 1994

[54] POLYMERIC X-RAY CONTRAST COMPOSITIONS CONTAINING AN ORGANIC CRYSTALLINE X-RAY CONTRAST AGENT

[75] Inventors: Carl R. Illig, Phoenixville; Eugene R. Cooper, Berwyn, both of Pa.

[73] Assignee: Sterling Winthrop Inc., Malvern, Pa.

[21] Appl. No.: 18,606

[22] Filed: Feb. 17, 1993

Related U.S. Application Data

[63] Continuation-in-part of Ser. No. 877,690, May 1, 1992.

[51] Int. Cl.$^5$ .................. A61K 49/04; A61K 31/715
[52] U.S. Cl. ........................................... 424/5; 424/4; 514/54; 514/57; 514/717; 514/941; 514/942; 514/580; 514/656; 568/580; 568/656
[58] Field of Search ............... 424/5, 4; 514/54, 57, 514/717, 941, 942, 580, 656; 568/580, 656

[56] References Cited

U.S. PATENT DOCUMENTS

| | | | |
|---|---|---|---|
| 2,622,100 | 12/1952 | Newbery | 260/612 |
| 2,659,690 | 6/1950 | Slaybaugh | 167/95 |
| 2,680,089 | 2/1950 | Lowy | 167/95 |
| 2,832,722 | 4/1958 | Singher | 167/95 |
| 3,192,118 | 6/1965 | Battista et al. | 167/95 |
| 4,038,379 | 7/1977 | Elinov et al. | 424/4 |
| 4,069,306 | 1/1978 | Rothman | 424/4 |
| 4,120,946 | 10/1978 | Queuille et al. | 424/4 |
| 4,588,574 | 5/1986 | Felder et al. | 423/554 |
| 4,692,325 | 9/1987 | Kritzler | 424/4 |
| 5,019,370 | 5/1991 | Jay et al. | 424/5 |

FOREIGN PATENT DOCUMENTS 55-127322 10/1980 Japan.

OTHER PUBLICATIONS

Wang et al. *Yaoxne Xuebao* 16(8):610–617 (1981).
James et al. Pharmaceutica Acta Helvetiae 47:244–256 (1972).

*Primary Examiner*—Gary E. Hollinden
*Attorney, Agent, or Firm*—Arthur Rosenstein; Imre (Jim) Balogh

[57] ABSTRACT

Disclosed are x-ray contrast compositions for oral or retrograde examination of the gastrointestinal tract comprising a polymeric material in combination with a divalent cation capable of forming a coating on the gastrointestinal tract and a crystalline contrast agent in a pharmaceutically acceptable carrier; and methods for their use in diagnostic radiology of the gastrointestinal tract.

7 Claims, No Drawings

POLYMERIC X-RAY CONTRAST COMPOSITIONS CONTAINING AN ORGANIC CRYSTALLINE X-RAY CONTRAST AGENT

CROSS REFERENCE TO RELATED APPLICATION

This is a continuation-in-part of appliction Ser. No. 07/877,690 filed on May 1, 1992.

BACKGROUND OF THE INVENTION

1. Field of the Invention

This invention relates to an x-ray contrast composition for oral or retrograde administration to a mammal comprising particles consisting essentially of a crystalline organic x-ray contrast producing agent and a polymeric film-forming material.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. The drawbacks of unevenly coating of the mucosa with an insufficiently adherence thereto proved to be rather difficult to solve. To that end, the use of certain polymer additives were proposed as illustrated hereunder.

U.S. Pat. No. 4,069,306 discloses an X-ray contrast preparation which is said to adhere to the walls of body cavities. The preparation comprises a finely divided water-insoluble inorganic X-ray contrast agent and minute particles of a hydrophilic polymer which is insoluble in water but is water-swellable. The body cavity is supplied with such preparation suspended in water. The X-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to X-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved X-ray imaging medium that uniformly coats the soft tissues subjected to diagnostic X-ray examination.

In U.S. patent application Ser. No. 07/938,786, we disclosed that the uniform coating of the mucosa of the intestine can be obtained by barium sulfate in combination with a film-forming material to provide high quality x-ray results.

We have now discovered that high quality x-ray results can be obtained by utilizing a formulation comprising x-ray contrast agent in solid, particulate form in combination with a film-forming material.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an X-ray emitting device, a polymeric film former, which has incorporated therein an organic x-ray contrast agent in particulate form, capable of coating the GI tract. Upon completion of the GI imaging examination, the removal of the coating occurs as a result of the normal turnover of cells, that is, within about 24 to 48 hours. Such compositions must meet several requirements: the film former must be nontoxic; must not contain leachable or digestible components that would deleteriously affect the patient; and the composition must be capable of forming a film in the pH range of from about 5 to about 8.

The object of the present invention is achieved by a composition comprising: an organic x-ray contrast agent in particulate form; a polymeric material which is at least partially water soluble and contains polarizable or ionizable groups; and a divalent metal ion selected from the group consisting of Mg++, Ca++, Zn++ and Ba++ which potentiates the effect of the polymeric material as a film former on the mucosa of the GI tract.

The organic x-ray contrast agent in particulate form, the polymeric film former and the divalent metal ion are incorporated in a solid or liquid media for administration to a mammal for X-ray visualization of the GI tract.

DETAILED DESCRIPTION OF THE INVENTION

Starting materials, reagents and solvents can be obtained from chemical suppliers, such as Aldrich, Baker, DuPont and Eastman Chemical Companies, or they may be prepared by techniques known in the prior art.

The polymers that were found to be suitable for forming a thin coating on the GI tract can be classified as anionic, cationic and neutral polymers, a description of which follows. U.S. Pat. No. 4,623,539, the disclosure of which is incorporated herein by reference, pertains to such polymers.

The x-ray contrast agent useful in the practice of this invention is nonradioactive and exists as a discrete, crystalline phase of an organic substance. The crystalline phase differs from an amorphous or non-crystalline phase which results from solvent precipitation techniques such as described in U.S. Pat. No. 4,826,689 noted above. The organic substance can be present in one or more suitable crystalline phases. The invention can be practiced with a wide variety of crystalline, non-radioactive x-ray contrast agents. However, the x-ray contrast agent must be poorly soluble and dispersible in at least one liquid medium. By "poorly soluble", it is meant that the agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media in which the selected x-ray contrast agent is poorly soluble and dispersible, including, for example, aqueous saline solutions, such as phosphate buffered saline (PBS), plasma, mixed aqueous and nonaqueous solutions, for example, water and alcohol, and suitable nonaqueous solvents such as alcohol, glycerol and the like.

The x-ray contrast agent can be an iodinated compound. The iodinated compound can be aromatic or nonaromatic. Aromatic compounds are preferred. The iodinated compound can comprise, one, two, three or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic acid, iothalamic acid, trimesic acid, urokonic acid, ioxaglic acid (hexabrix), ioxitalamic acid, tetraiodoterephthalic acid, iodipamide, icarmic acid, and the like.

Many of the iodinated molecules described above, if in monomeric form, can also be prepared as dimers (sometimes referred to as bis compounds), trimers (sometimes referred to as tris compounds), etc., by techniques known in the art. It is contemplated that this invention can be practiced with poorly soluble-iodinated compounds in monomeric, dimeric, trimeric and polymeric forms. Representative illustrative compounds are described by Sovak, cited above, pages 40–53.

Classes of preferred contrast agents have the following structural formulae:

A.

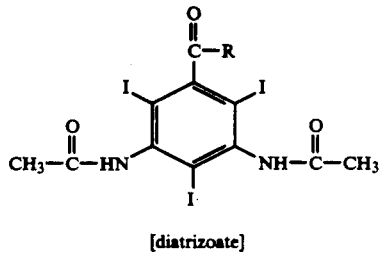

[diatrizoate]

B.

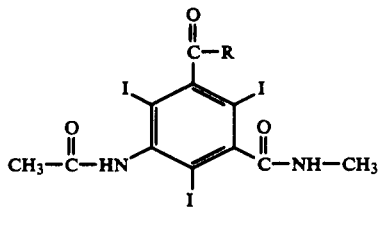

[iothalamate]

C.

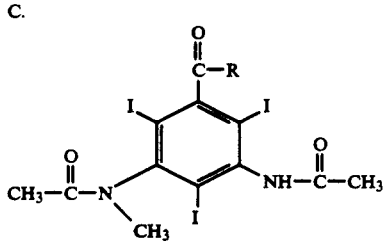

D.

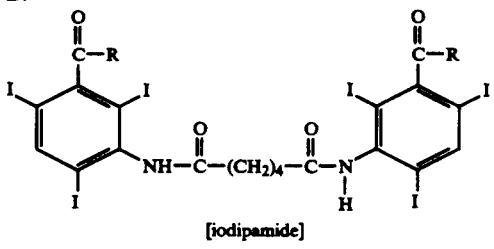

[iodipamide]

In the above structures, R can be OR$^1$,

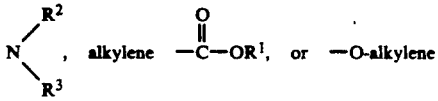

-continued

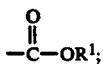

wherein R¹ is alkyl, and R² and R³ are independently H or alkyl.

Each alkyl group can independently contain from 1-20, preferably 1-8, and more preferably, 1-4 carbon atoms.

The alkylene group preferably contains from 1 to 4 carbon atoms such as methylene, ethylene, propylene and the like.

Particularly preferred contrast agents include the ethyl ester of diatiizoic acid, i.e., ethyl 3,5-diacetamido-2,4,6-triiodobenzoate, also known as ethyl 3,5-bis-(acetylamino)-2,4,6-triodobenzoate or ethyl diatrizoate, having the structural formula A above wherein R=—OCH$_2$CH$_3$ (WIN 8883); the ethyl glycolate ester of diatrizoic acid, i.e., ethyl (3,5-bis(acetylamino)-2,4,6-triiodobenzoyloxy)acetate, also known as ethyl diatrizoxyacetate, having the structural formula A above wherein

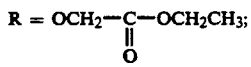

and ethyl 2-(3,5-bis(acetylamino)-2,4,6-triiodobenzoyloxy)butyrate, also known as ethyl 2-diatiizoxybutyrrate (WIN 16318).

In addition, the invention can be practiced in conjunction with the water insoluble iodinated carbonate esters described in PCT/EP90/00053.

The above described x-ray contrast agents are known compounds and/or can be prepared by techniques known in the art. For example, water-insoluble esters and terminal amides of acids such as the above-described iodinated aromatic acids can be prepared by conventional alkylation or amidation techniques known in the art. The above-noted acids and other acids which can be used as starting materials are commercially available and/or can be prepared by techniques known in the art. The examples which follow contain illustrative examples of known synthetic techniques.

EXAMPLE 1

Synthesis of Ethyl 3,5-bis(acetylamino)-2,4.6-triiodobenzoate

To 8.11 L of dry N,N-dimethylformamide was added 1.01 kg (1.65 mol) of diatrizoic acid. To the vigorously stirred suspension was carefully added 274 g (1.99 mol) of milled potassium carbonate. During the addition there was significant gas evolution. Before all of the suspended solid had gone into solution, a second solid began to form toward the end of the carbonate addition. The mixture was stirred for 30 min. at room temperature. Ethyl iodide (608 g, 3.90 mol) was added dropwise and the mixture was stirred overnight at room temperature at which point the reaction mixture was nearly homogeneous. The reaction was poured into 25 L of water, filtered and the solid washed with water and dried at reduced pressure at 60° C. to afford 962 g (91% yield) of a white solid, mp 280°–290° C. (dec.)

Analysis for C$_{13}$H$_{13}$I$_3$N$_2$O$_4$:

Calculated/Found: C, 24.32/24.27; H, 2.05/1.93; N, 4.36/4.28.

EXAMPLE 2

Synthesis of Ethyl (3,5-bis(acetylamino)-2,4,6-triiodo-benzoyloxy)acetate

To 175 mL of dry N,N-dimethylformamide (DMF) was added 63.6 g (0.100 mol) sodium diatrizoate and 14.7 g (0.120 mol) of ethyl chloroacetate and the mixture was heated on a steam bath for 6 hr. The reaction was filtered while hot and the filtrate cooled to room temperature and diluted to 500 ml with water. The mixture was cooled and filtered and the collected solid washed with water. The solid was then dissolved in 350 ml hot DMF, filtered and added to an equal volume of water. The mixture was cooled, filtered, washed with water, and the solid dried at 100° C. overnight to afford 53.0 g (76% yield) of a white powder, mp 269.5°–270.50° C.

Analysis for C$_{15}$H$_{15}$I$_3$N$_2$O$_6$:

Calculated/Found: C,25.73/25.80;H, 2.15/2.77; I, 54.4/53.8.

EXAMPLE 3

Synthesis of Ethyl 2-(3,5-bis(acetylamino)-2,4,6-triiodobenzoyloxy)butyrate

To 500 mL of dry N,N-dimethylformamide was added 159 g (0.250 mol) sodium diatrizoate and 54.5 g (0.280 mol) of ethyl 2-bromobutyrate. The mixture was heated on a steam bath for 20 h, cooled to room temperature and poured into 3 L of dilute ammonium hydroxide. The solid was filtered, washing with water, and air-dried. The solid was further purified by crystallization from 50% aqueous ethanol (after treatment with decolorizing carbon) affording two crops which were dried at 100° C. overnight to afford 121 g (66%) of a white powder, m.p. 288°–290° C. (dec.)

Analysis for C$_{17}$H$_{19}$I$_3$N$_2$O$_6$:

Calculated/Found: C, 28.05/28.36/ H, 2.63/2.55; I, 52.3/52.3

The particles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants. Representative examples of surface modifiers include gelatin, casein, lecithin (phosphatides), gum aeacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethyleellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP).

Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986, the disclosure of which is hereby incorporated by reference in its entirety.

Particularly preferred surface modifiers include polyvinylpyrrolidone, tyloxapol, poloxamers such as Pluronic F68 and F108, which are block copolymers of ethylene oxide and propylene oxide, and poloxamines such as Tetronic 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have been found to be particularly useful include Tetronic 908, the Tweens, Pluronic F-68 and polyvinylpyrrolidone. Other useful surface modifiers include:
decanoyl-N-methylglucamide;
n-decyl β-D-glucopyranoside;
n-decylβ-D-maltopyranoside;
n-dodecyl β-D-glucopyranoside;
n-dodecyl β-D-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glueopyranoside;
octanoyl-N-methylglucamide;
n-octyl β-D-glucopyranoside;
oetyl β-D-thioglucopyranoside;
and the like.

A particularly preferred class of surface modifiers includes water-soluble or water-dispersible compounds having the formula

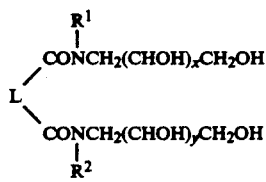

wherein

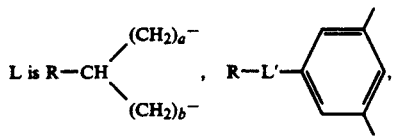

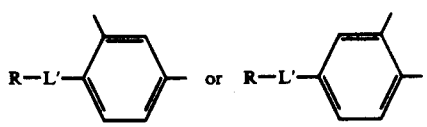

L' is a chemical bond, —O—, —S—, —NH—, —CONH—or —SO₂NH—;

R is a hydrophobic substituted or unsubstituted alkyl, substituted or unsubstituted cycloalkyl, or a substituted or unsubstituted aryl group;

each of $R^1$ and $R^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

Preferred compounds within this class conform to the above structure wherein R contains from 6 to 36 carbon atoms, for example, R is an n-alkyl group containing from 6 to 18 carbon atoms, each of $R^1$ and $R^2$ independently is a methyl, ethyl, propyl or butyl group and a is 0 and b is 0. This class of surface modifiers is described in U.K. Patent Application No. 9104957.7 filed Mar. 8, 1991 and can be prepared by reacting an appropriate dicarboxylic acid ester with an appropriate monosaccharide amine, preferably in the absence of a solvent, at a reaction temperature from 140° to 200° C.

The surface modifiers are commercially available and/or can be prepared by techniques known in the art. Two or more surface modifiers can be used in combination.

The particles useful in the practice of this invention can be prepared in accordance with the wet grinding process described in U.S. Pat. No. 5,145,684 which is incorporated herein by reference. The process comprises dispersing a poorly soluble x-ray contrast agent in a liquid dispersion medium and wet-grinding the agent in the presence of grinding media to reduce the particle size of the contrast agent to an effective average particle size of from about 0.05 μ to about 100 μ, preferably of from about 0.05 μ to about 5 μ and most preferably from about 0.1 μ to about 1 μ. The particles can be reduced in size in the presence of a surface modifier. Alternatively, the particles can be contacted with a surface modifier after attrition.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of from about 0.05 μ to about 100 μ" is meant that at least 90% of the particles have a weight average particle size of from about 0.05 μ to about 100 μ when measured by the above-noted techniques. The particle size range allows sufficient number of particles' distribution in the film forming composition when the GI tract is coated therewith, yet insures against absorption through the intestinal walls.

The contrast agent in particulate form, the polymeric material and divalent cation blend is then formulated for administration using physiologically acceptable carriers or excipients in a manner within the skill of the art. The contrast agent in particulate form, with the addition of pharmaceutically acceptable aids (such as surfactants and emulsifiers) and excipients may be suspended in an aqueous medium resulting in a dispersion, suspension or emulsion. Alternatively, the contrast agent in particulate form, the polymeric material and divalent cation may be formulated into a solid form, such as tablets or capsules.

Solid compositions of the present invention shall contain, instead of surfactants/emulsifiers and water used in the liquid compositions, bulking agents and other pharmaceutically acceptable ingredients advantageously employed to render the compositions palatable.

When the x-ray composition is formulated as a tablet, the bulking agent should have good compression characteristics. Suitable bulking agents are well known in the art and include a sweetener such as sugars, e.g. sucrose, and polyhydric alcohols, e.g. mannitol, sorbitol and xylitol, and mixtures thereof. When formulated as a tablet, it is preferable to incorporate in the composition one or more tablet lubricating agents, such as stearic acid, magnesium stearate and talc. The amount of the tablet lubricating agent as well as any other ingredients required to easily prepare the solid compositions, can readily be determined by the skilled formulator. The solid compositions may have incorporated therein optional pharmaceutically acceptable ingredients in order to impart thereto additional desirable properties, such as flavorants and colorants.

Compositions

Compositions of the present invention comprise the following pharmaceutically acceptable components based on % w/v:

| Polymeric Material | 0.001-25 |
| Divalent Cation | 0.001-20 |
| Contrast Agent | 5-95 |
| Excipient | 0-20 |
| Aids (Surfactants/Emulsifiers) | 0.01-20 |
| Water | q.s. to 100 |

Solid compositions of the present invention comprise the following pharmaceutically acceptable components based on % w/w:

| Polymeric Material | 0.001-25 |
| Divalent Cation | 0.001-20 |
| Contrast Agent | 5-95 |
| Bulking Agent/Lubricant/Flavor | q.s. to 100 |

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

Surfactants or emulsifiers can be used alone or in combination with other emulsifying agents and surfactants. For example, Dow Corning Medical Antifoam AF, which is a composition of 30% w/v polydimethylsiloxane and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 5% W/V of the aqueous formulations, although the amount, in general, is kept as low as possible, preferably in the range of 0.05 to 2% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuceinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the primary amide, monoethylamide and diethylamide of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:
(a) Sorbitan esters (sold under the trade name Span) having the formula:

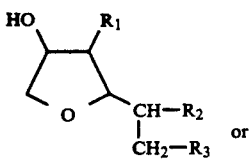

wherein
$R_1 = R_2 = OH$, $R_3 = R$ for sorbitan monoesters,
$R_1 = OH$, $R_2 R_3 = R$ for sorbitan diesters,
$R_1 = R_2 = R_3 = R$ for sorbitan triesters,
where $R = (C_{11}H_{23})$ COO for laurate,
$(C_{17}H_{33})$COO for oleate,
$(C_{15}H_{31})$COO for palmitate,
$(C_{17}H_{35})$COO for stearate;

(b) Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60;

(c) Polyoxyethylene sorbitan fatty acid esters, sold under the trade names of Polysorbates 20, 40, 60, 65, 80, and 85; and (d) Polyoxyethylene stearates, such as:
poly(oxy-1,2-ethanediyl)-α-hydro-ω-hydroxy-octadecanoate;
polyethylene glycol monostearate; and
poly(oxy- 1,2-ethanediyl)-α-(1-oxooctadecyl)ω-hydroxypolyethylene glycol monostearate.

The film former polymeric materials used in accordance with the present invention include anionic polymers, cationic polymers and neutral polymers.

I. Anionic Polymers

The anionic polymers carry negative charges in the ionized form and are capable of binding to cell surfaces mainly by electrostatic forces. Suitable anionic polymers include the following:

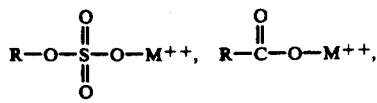

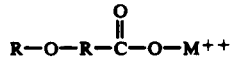

where
R is the polymeric chain;

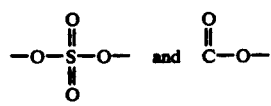

are anionic ligands; and $M^{++}$ is a divalent cation.

Specific anionic polymers useful in the practice of the present invention include:
(1) Sulfated polysacchaiides of the formula:

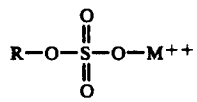

wherein R is 3,6-anhydro-D-galactose linked

| | |
|---|---|
| through C-4 to D-galactose; | (kappa carrageenan) |
| α-D-galactose units (1-3) linked; | (lambda carrageenan) |
| D-galactose | (iota carrageenan) |
| 3,6-anhydro-D-galactose; | |
| D-galactose | (Agar-Agar) |
| 3,6-anhydro-L-galactose; | |
| D-galactose | (Furcellaren) |
| 3,6-anhydro-D-galactose; | |
| D-glucopyranose; | (Laminarin sulfate) |
| Galactan; and | (Galactan sulfate) |
| Galactosamino-glucuronans and | (Chondroitin sulfates); |

$M^{++}$ is $Mg^{++}$, $Ca^{++}$, $Zn^{++}$, $Ba^{++}$ or mixtures thereof.

(2) Carboxylated polysaccharides of the formula:

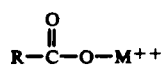

wherein R is
D-galacturonoglycan; and (Pectin)
anhydro-D-mannuronic acid
and anhydro-L-guluronic acid (Algin) residues; and
$M^{++}$ is $Mg^{++}$, $Ca^{++}$, $Zn^{++}$, $Ba^{++}$ or mixtures thereof.

(3) Cellulose derivatives of the formulae:

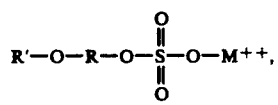

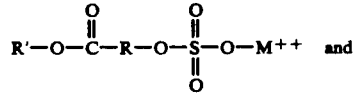

-continued $$R''{-}C{-}R{-}\overset{O}{\underset{\|}{C}}{-}O{-}M^{++}$$

wherein
R is an anhydroglucose residue;
R' is CH₃, C₂H₅ or C₃H₇;
R" is CH₃ or C₂H₅; and
M⁺⁺ is Mg⁺⁺, Ca⁺⁺, Zn⁺⁺, Ba⁺⁺ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

$$R{-}\overset{O}{\underset{\underset{O}{\|}}{\overset{\|}{S}}}{-}O{-}M^{++},\quad R{-}O{-}\overset{O}{\underset{\underset{O}{\|}}{\overset{\|}{S}}}{-}O{-}M^{++}\quad \text{and}$$

$$R{-}\overset{O}{\underset{\|}{C}}{-}O{-}M^{++}$$

wherein
R is an aliphatic or aromatic hydrocarbon, such as polystyrene, poly(sulfon) resin or carboxylated (poly) vinyl; and
M⁺⁺ is Mg⁺⁺, Ca⁺⁺, Zn⁺⁺, Ba⁺⁺ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as Mg⁺⁺, Ca⁺⁺, Zn⁺⁺ or Ba⁺⁺, the polymers are partially polarized thereby providing intermolecular interactions between the polymer and the intestinal wall. Examples of these polymers include:
 (a) Polysaccharides, such as starch, glycogen, glucan, fructans, mannans, galactomannas, glucomannas, galactans, xylans, glycuranans, dextran and starch amylose;
 (b) Cellulose derivatives, such as methylcellulose, hydroxyethylcellulose, ethylhydroxyethyl cellulose, hydroxypropyl methylcellulose and hydroxypropyl cellulose; and
 (c) Synthetic polymers, such as polyvinylpyrrolidone, polyvinyl alcohol and ethylene oxide polymers.

Exemplary formulations of the present invention are as shown:

EXAMPLE 4

| Ethyl Diatrizoate | 1.94 g (19.4% w/v) |
|---|---|
| Dow Corning Med. Antifoam AF emulsion | 1.50 g (15% w/v) |
| Tween 80 | 0.35 g (3.5% w/v) |
| Galactan Sulfate | 0.3 g (3% w/v) |
| Calcium Lactate | 0.3 g (3% w/v) |
| Purified Water | q.s. to 10 ml |

EXAMPLE 5

| Ethyl Diatrizoate | 1.50 g (15.0% w/v) |
|---|---|
| Tetronic 908 | 0.45 g (4.5% w/v) |
| Sodium Carrageenan | 2.50 g of 2% (w/v) solution |
| Calcium Lactate | 0.3 g (3% w/v) |
| Purified Water | q.s. to 10 ml |

EXAMPLE 6

| Ethyl Diatrizoxyacetate | 2.00 g (2.00% w/v) |
|---|---|
| Mineral Oil | 0.50 g (5% w/v) |
| Heparin | 0.25 g (2.5% w/v) |
| Tween 21 | 0.25 g (2.5% w/v) |
| Pluronic F-68 | 0.40 g (4.0% w/v) |
| Calcium Lactate | 0.25 g (2.5% w/v) |
| Purified Water | q.s. to 10 ml |

EXAMPLE 7

| Ethyl 2-(3,5-bis(acetylamino)-2,4,6-triiodobenzoyl butyrate | 1.80 g (18.0% w/v) |
|---|---|
| Simplesse 100 (Nutrasweet Co.) | 3.00 g (30% w/v) |
| Magnesium Citrate | 0.5 (5% w/v) |
| Span 80 | 0.4 g (4% w/v) |
| Hydroxypropyl methylcellulose (4000 cPs) | 2.50 g of 2% (w/v) solution |
| Purified Water | q.s. to 10 ml |

The compositions of the invention may be administered orally to the patient for radiological examination of the GI tract. The compositions of the invention may also be administered rectally in the form of enemas to a patient for radiologic examination of the colon.

The dosages of the contrast agent used according to the method of the present invention will vary according to the precise nature of the ingredients used. Preferably, however, the dosage should be kept as low as is consistent with achieving contrast enhanced imaging. By employing as small amount of the composition as possible, toxicity potential is minimized. For most formulations of the present invention dosages will be in the range of from about 0.1 to about 20.0 g I/kg body weight, preferably in the range of from about 0.4 to about 8.0 g I/kg of body weight, and most preferably, in the range of from about 1.0 to about 3.0 g I/kg body weight for regular X-ray visualization of the GI tract. For CT scanning the contrast agents of the present invention will be in the range of from about 1 to about 800 mg I/kg body weight, preferably in the range of from about 15 to about 250 mg I/kg body weight, and most preferably in the range of from about 35 to about 90 mg I/kg body weight.

The concentration of the contrast agent should be in the range of from about 5% w/w to about 95% w/w of the formulation, preferably from about 10% w/w to about 60% w/w and most preferably of from about 15% w/w to about 40% w/w.

The concentration of the film forming polymeric material depends on the particular polymer used, however, it should be in the range of 0.01 to about 25% w/w or higher in combination with a divalent substance, such as calcium lactate, having a concentration range of 0.001 to 20% w/w of the cationic element. Dosage level of the polymeric material may be in the range of from about 2 to about 20 g/kg body weight or higher.

The compositions of the present invention possess very good adherence to the walls of the gastrointestinal tract by forming an essentially uniform coating thereon.

The invention, having been fully described, it will be apparent to one skilled in the art that changes and modi-

What is claimed is:

1. An x-ray contrast composition designed for depositing a thin, flexible film membrance onto the mucosal lining of the nutrient absorbing inner surface of the intenstine of a patient to form a barrier between said nutrient absorbing inner surface and the content of said intestine, said flexible film membrane to remain bound to said mucosal lining until eliminated by normal cell turnover comprising based on w/v:

(a) of from about 0.1 to about 25% of a polymeric material capable of forming a film membrane on the gastrointestinal tract in the pH range of from about 5 to about 8, said polymeric material being selected from the group consisting of anionic polymers carrying negative charges in the ionized form, cationic polymers carrying positive charges in the ionized form, and neutral polymers, said neutral polymers having atoms containing polarizable electrons thereon, selected from the group consisting of oxygen, nitrogen, sulfur, fluoride, chloride, bromide and iodide, in combination with (b) of from about 0.1 to about 20% of a divalent cation to potentiate the binding of said flexible film membrane to said mucosal lining selected from the group consisting of $Ca^{++}$, $Mg^{++}$, $Zn^{++}$ and $Ba^{++}$; and (c) of from about 5 to about 95% of a crystalline contrast agent having a surface modifier adsorbed on the surface thereof in an amount sufficient to maintain an effective average particle size of from about 0.5 μ to about 100 μ in a pharmaceutically acceptable carrier wherein said crystalline contrast agent is selected from the group consisting of diatrizoic acid, metrizoic acid, iothalamic acid, trimesic acid, urokocic acid, ioxathalamic acid, tetraiodoterephthalic acid, ioxaglic acid, iodipamide, ethyl-3,5-diacetamido-2,4,6-triiodobenzoate, ethyl-2-(3,5-bis(acetylamino)-2,4,6-triiodobenzoyloxy)butyrate, and ethyl(3,5-bis(acetylamino)-2,4,6Øtriiodobenzoyloxy)-acetate; and said surface modifier is selected from the group consisting of a tetrafuctional block copolymer derived from sequential addition of propylene oxide and ethylene oxide to ethylenediamine, and a compound of the formula $$\begin{array}{c} R^1 \\ | \\ CONCH_2(CHOH)_xCH_2OH \\ L \\ CONCH_2(CHOH)_yCH_2OH \\ | \\ R^2 \end{array}$$

wherein

L is $R-CH\begin{array}{c}(CH_2)_a{}^- \\ (CH_2)_b{}^-\end{array}$, $R-L'-\text{[phenyl]}$, $R-L'-\text{[phenyl]}$ or $R-L'-\text{[phenyl]}$, L' is a chemical bond, —O—, —S—, —NH—, —CONH— or —$SO_2NH$—;

R is a hydophobic substituted or unsubstituted alkyl, substituted or unsubstituted cycloalkyl, or a substituted or unsubstituted aryl group;

each of $R^1$ and $R^2$ independently is hydrogen or an alkyl group having from 1 to 4 carbon atoms;

each of a and b independently is 0 or an integer from 1 to 3, provided that the sum of a and b is not greater than 3; and each of x and y independently is an integer from 3 to 7.

2. The x-ray contrast composition of claim 1 wherein said anionic polymeric material is a sulfated polysaccharide having the formula:

$$R-O-\underset{\underset{O}{\|}}{\overset{\overset{O}{\|}}{S}}-O-M^{++}$$

wherein R is 3,6-anhydro-D-galactose

| | |
|---|---|
| through C-4 to D-galactose; | (kappa carrageenan); |
| α-D-galactose units (1-3) linked; D-galactose; | (lambda carrageenan);] |
| [3,6-anhydro-D-galactose; D-galactose] | (iota carrageenan) |
| 3,6-anhydro-L-galactose [: D-galactose | (Agar-Agar)]; |
| [3,6-anhydro-D-galactose; D-glucopyranose; Galactan; and Galactosamino-glucuronans and | (Furcellaren) (Laminarin sulfate)] [(Galactan sulfate)] [(Chondroitin sulfates);] |
| $M^{++}$ is $Mg^{++}$, $Ca^{++}$, $Zn^{++}$, $Ba^{++}$ or a mixture thereof.— | |

3. The x-ray contrast composition of claim 1 wherein said anionic polymeric material is a sulfated, sulfonated or carboxylated synthetic polymer having the formula:

$$R-\underset{\underset{O}{\|}}{\overset{\overset{O}{\|}}{S}}-O-M^{++}, \quad R-O-\underset{\underset{O}{\|}}{\overset{\overset{O}{\|}}{S}}-O-M^{++},$$

$$-R-\overset{\overset{O}{\|}}{C}-O-M^{++}$$

wherein

R is an aliphatic or aromatic hydrocarbon; and $M^{++}$ is $Mg^{++}$, $Ca^{++}$, $Zn^{++}$, $Ba^{++}$ or a mixture thereof.

4. The x-ray contrast composition of claim 1 wherein said cationic polymeric material is selected from the group consisting of: dermatan sulfate, keratosulfate, hyaluronic acid, heparin and chitin.

5. The x-ray contrast composition of claim 1 wherein said pharmaceutical carrier contains at least one surfactant.

6. The x-ray contrast formulation of claim 5 wherein said cationic surfactant is selected from the group consisting of cetyltrimethyl ammonium bromide, dodecyl dimethyl ammonium bromide, sodium lauryl sulfate, sodium heptadecyl sulphate, an alkyl benzene sulphonic acid, sodium butylnaphthalene sulfonate, sodium butylnaphthalene, sulphosuccinate, carboxylic esters, carboxylic amides, ethoxylated alkylphenols, ethoxylated aliphatic alcohols, polyoxyethylene alkyl ethers, polyoxyethylene sorbitan fatty acid esters and zwitterionic surfactants.

7. A method of carrying out x-ray examination of the gastrointestinal tract of a patient, said method comprises the oral or rectal administration to the patient an x-ray contrast composition according to claim 1.

* * * * *